(12) United States Patent
Horton et al.

(10) Patent No.: US 6,190,402 B1
(45) Date of Patent: *Feb. 20, 2001

(54) INSITU FORMABLE AND SELF-FORMING INTRAVASCULAR FLOW MODIFIER (IFM) AND IFM ASSEMBLY FOR DEPLOYMENT OF SAME

(75) Inventors: Joseph A. Horton, Charleston; Diana Joan Vincent, Folly Beach, both of SC (US)

(73) Assignee: Musc Foundation for Research Development, Charleston, SC (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/668,229

(22) Filed: Jun. 21, 1996

(51) Int. Cl.[7] .................................................. A61F 2/06
(52) U.S. Cl. ................................ 623/1; 623/12; 606/198; 606/108
(58) Field of Search .................................. 606/108, 198, 606/191, 195; 623/1, 12

(56) References Cited

U.S. PATENT DOCUMENTS

| | | |
|---|---|---|
| D. 359,802 | 6/1995 | Fontaine . |
| 3,868,956 | * 3/1975 | Alfidi et al. ............... 606/198 X |
| 4,512,338 | 4/1985 | Balko et al. . |
| 4,553,545 | * 11/1985 | Maas et al. ................. 606/198 |
| 4,655,771 | 4/1987 | Wallsten . |
| 4,768,507 | * 9/1988 | Fischell et al. ............. 606/108 |
| 4,994,069 | * 2/1991 | Ritchart et al. ............. 606/191 |
| 5,015,253 | 5/1991 | Macgregor . |
| 5,019,090 | * 5/1991 | Pinchuk ..................... 606/108 X |
| 5,035,706 | 7/1991 | Giantureo et al. . |
| 5,041,126 | * 8/1991 | Giantureo .................. 606/195 |
| 5,116,365 | 5/1992 | Hillstead . |
| 5,135,536 | 8/1992 | Hillstead . |
| 5,171,262 | 12/1992 | Macgregor . |
| 5,192,297 | 3/1993 | Hull . |
| 5,197,978 | 3/1993 | Hess . |
| 5,256,146 | * 10/1993 | Ensminger et al. ............. 604/106 X |
| 5,304,200 | 4/1994 | Spaulding . |
| 5,342,300 | 8/1994 | Stefanadis et al. . |
| 5,383,887 | 1/1995 | Nadal . |
| 5,395,390 | 3/1995 | Simon et al. . |
| 5,405,377 | 4/1995 | Cragg . |
| 5,415,664 | 5/1995 | Pinchuk . |

(List continued on next page.)

FOREIGN PATENT DOCUMENTS

| | | |
|---|---|---|
| 0 518 704 A1 | 12/1992 | (EP) . |
| 0 627 201 A1 | 12/1994 | (EP) . |
| 9214408 | * 9/1992 | (WO) .................... 606/198 |
| 9416629 | * 8/1994 | (WO) .................... 606/108 |
| WO 95/18585 | 7/1995 | (WO) . |

OTHER PUBLICATIONS

Copy of International Search Report Relating to PCT/US97/10882 Dated Nov. 6, 1997.

Primary Examiner—Michael H. Thaler
(74) Attorney, Agent, or Firm—Fulwider Patton Lee & Utecht, LLP

(57) ABSTRACT

An intravascular flow modifier (IFM) for use in a vessel has an outer layer formed of a strand configured as a longitudinally oriented coil of adjacent helical loops extending between a first end and a second end of the outer layer. The outer layer is secured in the vessel by at least some of the helical loops pressing against a portion of the interior surface of the vessel. The IFM also has an inner layer formed of a strand configured as a longitudinally oriented coil of adjacent helical loops extending between a first end and a second end of the inner layer. At least a portion of the outer layer surrounds at least a portion of the inner layer so that at least some of the loops of the outer layer overlap and contact at least some of the loops of the inner layer An assembly and method for deploying are also disclosed.

48 Claims, 7 Drawing Sheets

U.S. PATENT DOCUMENTS

| | | |
|---|---|---|
| 5,433,723 | 7/1995 | Lindenberg et al. . |
| 5,476,505 | 12/1995 | Limon . |
| 5,480,423 | 1/1996 | Ravenscroft et al. . |
| 5,484,449 * | 1/1996 | Amundson et al. ............. 606/198 X |
| 5,540,701 * | 7/1996 | Sharkey et al. .................. 606/198 X |
| 5,609,627 * | 3/1997 | Goicoechea et al. .................... 623/1 |
| 5,613,981 * | 3/1997 | Boyle et al. ......................... 606/198 |
| 5,716,410 | 2/1998 | Wang et al. . |
| 5,980,514 | 11/1999 | Kupiecki et al. . |

* cited by examiner

INSITU FORMABLE AND SELF-FORMING INTRAVASCULAR FLOW MODIFIER (IFM) AND IFM ASSEMBLY FOR DEPLOYMENT OF SAME

BACKGROUND OF THE INVENTION

1. Field of the Invention

The present invention relates broadly to an insitu formable and self-forming intravascular flow modifier (IFM) and/or stent and the delivery and deployment of the IFM to a defect in a vessel. More particularly, the invention relates to an IFM that may be deployed in previously inaccessible vessels to current generation IFMs or stents due to the nearly linear pre-deployed configuration of the IFM and a method for controlling the final placement and deployed configuration of the IFM within a pre-selected segment of the vessel. The present invention is particularly suited but not limited to use as an intracranial IFM and method for deploying the IFM in a vessel.

2. Description of the Related Art

Most related art devices cannot be deployed in intracranial vessels. Even the devices having a pre-deployed configuration with a substantially reduced diameter compared to their respective deployed configuration are typically too large and too stiff to navigate the tight turn of the carotid artery and other small vessels of the body with torturous turns.

U.S. Pat. No. 4,512,338 issued to Balko et al. discloses a process of deploying a memory metal coil across a defect in a vessel. The coil is elongated prior to deployment and warmed within the vessel to substantially revert back to its original coil form.

None of the related art, including Balko et al., discloses IFM or a stent having the radial strength associated with multiple coils within one another with the capability of deploying the IFM or stent with a deployed configuration variably controlled by the relative movement of the strand forming the IFM or stent and a catheter through which the strand extends.

A need exists for an IFM, a catheter and IFM assembly, and a method for deploying the IFM which can provide a coil-in-coil IFS of various deployed configurations in previously inaccessible vessels according to the judgement of the physician at the time of deployment.

SUMMARY OF THE INVENTION

Accordingly, the present invention is directed to an IFM, a catheter and IFM assembly, and a method for deploying the IFM that overcomes the limitations and disadvantages of the related art.

An advantage of the present invention is its simple design that is nevertheless capable of providing an IFM that may be readily deployed in various configurations according to the specific vessel defect to alter the flow dynamics of the vessel, to keep an embolus deployed in a wide neck aneurysm in the aneurysm, or to support and strengthen the vessel.

Another advantage is that the IFM can access vessels through a unique catheter assembly and associated technique for delivering the IFM in a manner previously unavailable in the related art.

Additional features and advantages of the invention will be set forth in the description which follows, and in part will be apparent from the description, or may be learned by practice of the invention. The objects and other advantages of the invention will be realized and attained by the IFM, the catheter and IFM assembly, and the method for deploying the IFM particularly pointed out in the written description and claims hereof as well as the appended drawings.

To achieve these and other advantages in accordance with the purpose of the invention, as embodied and broadly described, the invention comprises an outer layer formed of a strand, which is configured as a longitudinally oriented coil of adjacent helical loops extending between a first end and a second end of the outer layer. The outer layer is secured in the vessel by at least some of the helical loops pressing against a portion of the interior surface of the vessel. The invention also includes an inner layer formed of a strand, which is configured as a longitudinally oriented coil of adjacent helical loops extending between a first end and a second end of the inner layer. At least a portion of the outer layer surrounds at least a portion of the inner layer so that at least some of the loops of the outer layer overlap and contact at least some of the loops of the inner layer.

Preferably, the strand of the outer layer and the inner layer is a continuous strand, which is more preferably formed of or coated by a biocompatible material. Preferably, the strands of the outer and inner layers are formed of a high shape memory alloy, such as Nitinol alloy. The strand of the outer layer and the strand of the inner layer preferably have a circular, oval, rectangle, or triangular cross-section.

In one embodiment of the invention, the second end of the outer layer is anchored proximal to the first end of the inner layer. The second end of the outer layer preferably joins the first end of the inner layer. In another embodiment of the invention, the first end of the outer layer attaches to the second end of the inner layer so that the continuous strand forms a loop.

The first end of the outer layer and the second end of the inner layer may include means for inhibiting the wire strand from penetrating through the interior surface of the vessel, such as a loop on the ends. The first end of the outer layer and the second end of the inner layer are preferably distal ends relative to an insertion point into the vessel. The second end of the outer layer and the first end of the inner layer are preferably proximal ends relative to an insertion point into the vessel. Alternatively, the respective ends of the outer and inner layers may be reversed relative to the insertion point into the vessel depending upon the method used to deploy the IFM.

The preferred helical loops of the outer and inner layers are substantially circular. Both the helical loops of the outer and inner layers wind in a predetermined direction. Preferably, the rotation of the helical loops of the outer and inner layers is in the same direction but with the helical loops of the outer layer having a alpha helix and the helical loops of the inner layer having a beta helix. Of course, the outer layer may have the beta helix and the inner layer may have the alpha helix. Preferably, the number of helical loops of the outer layer is N, where N is at least two, and the number of the helical loops of the inner layer is M, where M is at least two.

In another embodiment of the invention, the outer layer is divided into at least a first end portion, a middle portion, and second end portion along the longitudinally oriented coil. The first end, middle, and second end portions each have a pitch. The pitch of the middle portion may be smaller than the pitch of the first end and second end portions. Alternatively, the pitch of the middle portion may be larger than the pitch of the first end and second end portions. The pitch of the first and second end portions preferably provides a gap between the helical loops of between 3 and 7 mm (0.118 and 0.276 inches), while the pitch of the middle portion preferably provides a gap between the helical loops of between 0.5 and 3 mm (0.020 and 0.118 inches).

The diameter of the wire strand of the first end and second end portions of the outer layer may be smaller than the diameter of the wire strand of the middle portion. A preferred diameter of the wire strand of the outer layer is no greater than 0.020 inches. A more preferred diameter of the wire strand of the outer layer is between 0.00025 and 0.006 inches. The diameter of the wire strand of the outer layer comprising the first end and second end portions is more preferably between 0.001 and 0.002 inches, and the diameter of the wire strand comprising the middle portion is more preferably between 0.003 and 0.004 inches.

As with the outer layer, the inner layer may be divided into at least a first end portion, a middle portion, and a second end portion along the longitudinally oriented coil. The pitch of the middle portion may be smaller than the pitch of the first end and second end portions. Alternatively, the pitch of the middle portion may be larger than the pitch of the first end and second end portions. The pitch of the first and second end portions preferably provides a gap between the helical loops of between 3 and 7 mm, while the pitch of the middle portion preferably provides a gap between the helical loops of between 0.5 and 3 mm.

The diameter of the wire strand of the first end and second end portions of the inner layer may be smaller than the diameter of the wire strand of the middle portion. A preferred diameter of the wire strand of the inner layer is no greater than 0.020 inches. A more preferred diameter of the wire strand of the inner layer is between 0.00025 and 0.006 inches. The diameter of the wire strand of the inner layer comprising the first end and second end portions is more preferably between 0.001 and 0.002 inches, and the diameter of the wire strand comprising the middle portion is more preferably between 0.003 and 0.004 inches. The helical loops of the inner layer preferably have a substantially constant inner diameter.

An alternative embodiment of the present invention may include a second inner layer formed of a strand, which is configured as a longitudinally oriented coil of adjacent helical loops extending between a first end and a second end of the second inner layer. At least a portion of the first inner layer surrounds at least a portion of the second inner layer so that at least some of the loops of the first inner layer overlap and contact at least some of the loops of the second inner layer.

The invention also comprises a continuous length of wire strand formed as a longitudinally oriented coil surrounding another longitudinally oriented coil. The coils form an outer layer of adjacent helical loops surrounding an inner layer of adjacent helical loops. The outer layer urges against a portion of the interior surface of the vessel. The helical loops of the inner layer urge against the loops of the outer layer at crossing points.

Another embodiment of the invention for use in a cranial vessel comprises an outer layer formed of a strand having a first end, a second end opposite the first end, and a longitudinally oriented coil of adjacent helical loops between the first and second ends. The outer layer is secured in the cranial vessel by at least some of the helical loops pressing against a portion of the interior surface of the vessel. An inner layer formed of a strand of wire has a first end, a second end opposite the first end, and a longitudinally oriented coil of adjacent helical loops between the first and second ends. At least a portion of the outer layer surrounds at least a portion of the inner layer so that at least some of the loops of the outer layer overlap and contact at least some of the loops of the inner layer. The wire strand of the outer and inner layers is a continuous strand form of a high shape memory alloy. The helical loops of the outer an inner layers are substantially circular. The second end of the outer layer joins the first end of the inner layer. The first end of the outer layer and second end of the inner layer have distal ends relative to an insertion point into the vessel. The second end of the outer layer and first end of the inner layer are proximal ends relative to an insertion point into the vessel. Additionally the IFM has an outside diameter of between about 1.5 and 12 mm (0.059 and 0.472 inches)

Yet another embodiment of the invention comprises at least one outer helical loop formed of a strand of wire. The outer loop is secured in the vessel by at least some portion of the helical loop pressing against a portion of the interior surface of the vessel. The invention also comprises at least one inner helical loop formed of a strand of wire. At least some portion of the outer helical loop surrounds at least a portion of the inner helical loop so that at least some of the outer helical loop overlaps and contacts at least some of the inner helical loop. Preferably, the outer helical loop overlaps and contacts the inner helical loop at a crossing point. More preferably, at least one crossing point is adjacent to the defect in the interior of the vessel.

The invention also includes an assembly for an intravascular repair of a defect of a body vessel. The assembly comprises an elongated first catheter and an IFM having a deployed configuration when in the vessel at a site of the defect and a pre-deployed configuration for movement through the first catheter. The IFM includes an outer layer and an inner layer as discussed above. The first catheter has a proximal end, a distal end, and a central lumen extending axially therethrough. The lumen has a size and shape complementary to the pre-deployed configuration of the IFM such that the IFM is axially slidable therethrough. A preferred first catheter has an outside diameter of between about 0.010 and about 0.014 inches and an inside diameter of between about 0.004 and about 0.006 inches.

The assembly may further include a second catheter having a distal end, a proximal end, and a central lumen extending axially therethrough. The lumen of the second catheter has a size and shape complementary to the first catheter such that the first catheter is axially slidable therein. At least a portion of the distal end of the first catheter can be inserted into the lumen of the second catheter at the proximal end and passes through the lumen of the second catheter and exits the second catheter at the distal end. A preferred second catheter has an outside diameter of approximately 1 mm (0.03937 inches) and an inside diameter of at least approximately 0.022 inches.

The assembly preferably includes a third catheter having a distal end, a proximal end, and a central lumen extending axially therethrough. The lumen of the third catheter has a size and shape complementary to the second catheter such that the second catheter is axially slidable therein. At least a portion of the distal end of the second catheter can be inserted into the lumen of the third catheter at the proximal end and passes through the lumen of the third catheter and exits the third catheter at the distal end.

Another embodiment of the assembly comprises an IFM having a deployed configuration when in the vessel at a site of the defect and a pre-deployed configuration for movement through the vessel towards the site of the defect as discussed above. The assembly also includes a means for moving and maintaining the IFM when in the pre-deployed configuration. The outer and inner layers of the IFM take the deployed configuration when the moving and maintaining means is no longer applied thereto. The moving and maintaining means preferably comprises an elongated first catheter having a size and shape complementary to the respective size and shape of the IFM when in the pre-deployed configuration so that the outer and inner layers are axially slidable therein.

Alternatively, the assembly may include means for disposing the IFM within the vessel. The disposing means preferably comprises an elongated first catheter as with the moving and maintaining means above, but also includes an elongated second catheter having a size and shape complementary to the first catheter such that the first catheter is axially slidable therein. At least a portion of the distal end of the first catheter can be inserted into the lumen of the second catheter at the proximal end and passes through the lumen of the second catheter and exits the second catheter at the distal end.

The assembly may further include means for selectively varying the gap between the adjacent helical loops of the outer and inner layers. The preferred selectively varying means includes an elongated first catheter and an elongated second catheter as just discussed, but also includes means for controlling axial movement of the IFM when in the pre-deployed configuration through the first catheter and out of the distal end of the first catheter. The controlling means preferably includes means for controlling the axial movement of both the IFM and the first catheter.

Finally, the present invention also includes a method of forming an IFM having a first portion comprising an outer layer of strand and a second portion comprising an inner layer of strand at a pre-selected segment of a vessel. The method comprises the steps of moving the IFM through a catheter up to the pre-selected segment of the vessel; manipulating at least one of the outer layer of strand and the catheter to deploy the outer layer of strand in the pre-selected segment of vessel as a longitudinally oriented coil of adjacent helical loops; and manipulating at least one of the inner layer of strand and the catheter to deploy the inner layer of strand in the pre-selected segment of vessel as a longitudinally oriented coil of adjacent helical loops within the first portion of the IFM.

The step of moving preferably includes the step of insulating the IFM within the catheter. The method may also include the step of inserting the IFM into the catheter prior to the step of moving. Further, the method may include the step of elongating the IFM prior to inserting the IFM into the catheter. The step of elongating the IFM preferably includes the step of straightening the IFM to a substantially linear configuration.

The preferred catheter used in the step of moving has a size and shape complementary to the IFM when elongated such that the first and second portions of the IFM are axially slidable therethrough. The same catheter is preferred for used in the step of inserting and may be referred to as a micro-catheter. The step of inserting may further include the step of providing an elongated guide catheter having a size and shape complementary to the micro-catheter such that the micro-catheter is axially slidable therethrough. The guide catheter is preferably positioned in the vessel with the distal end of the guide catheter being oriented near the pre-selected segment of the vessel. The method may further include the step of inserting at least a portion of the distal end of the micro-catheter into the lumen of the guide catheter at the proximal end and passing through the lumen of the guide catheter and exiting the guide catheter at the distal end prior to the step of moving the IFM.

The step of inserting preferably further comprises the step of providing an elongated angiographic catheter having a size and shape complementary to the guide catheter such that the guide catheter is axially slidable therethrough. The angiographic catheter is preferably positioned in the vessel with the distal end of the angiographic catheter oriented closer to an insertion point into the vessel than the distal end of the guide catheter. The method preferably includes the step of inserting at least a portion of the distal end of the guide catheter into the lumen of the angiographic catheter at the proximal end and passing through the lumen of the angiographic catheter and exiting the angiographic catheter at the distal end prior to the step of moving the IFM.

A method of practicing the method includes the step of inserting the angiographic catheter into the vessel before inserting the guide catheter containing and the micro-catheter into the vessel. The method preferably also includes the steps of halting the advancement of the angiographic catheter into the vessel and continuing to advance the guide catheter containing the micro-catheter into the vessel, and the steps of halting the advancement of the guide catheter into the vessel and continuing to advance the micro-catheter into the vessel.

In one embodiment of the method, the steps of manipulating include the steps of selectively varying the spacing between the adjacent helix loops of the outer and inner layers, respectively. The method may further include the step of expanding the IFM substantially to a pre-elongated diameter during the steps of manipulating. The step of expanding the IFM preferably includes the step of warming the wire strand of the outer layer and the wire strand of the inner layer. For strands that are not formed of temperature responsive memory metals, the catheter within which the strand is moved mechanically constrains the strand from resuming its coiled diameter until released from the catheter. Regardless of the material used to form the strand, the catheter preferably has the structural characteristics to permit a user to pull the strand back into the catheter prior to final deployment.

The step of manipulating at least one of the outer layer and the catheter preferably includes the step of providing the outer layer with a number of loops where the number is at least two. Alternatively, the step of manipulating at least one of the outer layer and the catheter may include the step of providing the outer layer with a single loop. The step of manipulating at least one of the inner layer and the catheter preferably includes the step of providing the inner layer with a number of loops where the number is at least two. Alternatively, the step of manipulating at least one of the inner layer and the catheter may include the step of providing the inner layer with a single loop.

The step of manipulating first portion of the IFM includes the step of producing the outer layer with the portions, pitch, winding, and gap criteria from the IFM discussion above. The step of manipulating the outer layer or first portion of the IFM preferably includes the step of pushing the first portion out of the catheter and into the pre-selected segment. More preferably, the step of pushing includes pushing the first portion out of the distal end of the catheter while pulling the catheter towards the insertion point into the vessel. Alternatively, the step of pushing may include pushing the first portion out of the distal end of the catheter at a predetermined rate while pushing the catheter towards the pre-selected segment of the vessel at a rate slower than the predetermined rate of the first portion.

The step of manipulating the second portion of the IFM includes the step of producing the inner layer with portions, pitch, winding, and gap criteria from the IFM discussion above. The step of manipulating the inner layer or second portion of the IFM preferably includes the step of pushing the second portion out of the catheter and into the pre-selected segment. More preferably, the step of pushing includes pushing the second portion out of the distal end of the catheter at a predetermined rate while pushing the catheter towards the pre-selected segment of the vessel at a rate slower than the predetermined rate of the second portion. Alternatively, the step of pushing may include pushing the second portion out of the distal end of the catheter while pulling the catheter towards the insertion point into the vessel.

A preferred method of practicing the present invention includes the steps of straightening the IFM to a substantially linear configuration; providing an angiographic catheter, a guide catheter, and a micro-catheter, each of the catheters having a distal end, a proximal end, and a central lumen extending axially therethrough; inserting the angiographic catheter into the vessel; inserting the micro-catheter into the guide catheter, and the guide catheter into the angiographic catheter; inserting the IFM into the micro-catheter; positioning the distal end of the angiographic catheter at a predetermined location in the vessel proximal to the pre-selected segment of the vessel; advancing at least a portion of the distal end of the guide catheter through the angiographic catheter and exiting the angiographic catheter at the distal end; positioning the guide catheter in the vessel with the distal end of the guide catheter being oriented between the pre-selected segment of the vessel and the distal end of the angiographic catheter; advancing at least a portion of the distal end of the micro-catheter through the guide catheter and exiting the guide catheter at the distal end; moving the IFM through the micro-catheter up to the pre-selected segment of the vessel; manipulating at least one of the outer layer of strand and the catheter to deploy the outer layer of strand in the pre-selected segment of vessel as a longitudinally oriented coil of adjacent helical loops; and manipulating at least one of the inner layer of strand and the catheter to deploy the inner layer of strand in the pre-selected segment of vessel as a longitudinally oriented coil of adjacent helical loops within the first portion of the IFM.

Another method of practicing the present invention includes the steps of straightening the IFM to a substantially linear configuration; providing a guide catheter and a micro-catheter, each of the catheters having a distal end, a proximal end, and a central lumen extending axially therethrough; inserting the micro-catheter into the guide catheter; inserting the guide catheter into the vessel; inserting the IFM into the micro-catheter; positioning the guide catheter in the vessel with the distal end of the guide catheter being oriented between the pre-selected segment of the vessel and an insertion point into the vessel; advancing at least a portion of the distal end of the micro-catheter through the guide catheter and exiting the guide catheter at the distal end; moving the IFM through the micro-catheter up to the pre-selected segment of the vessel; and manipulating the layer of strand and the catheter to deploy the layer of strand in the pre-selected segment of vessel as a longitudinally oriented coil of adjacent helical loops.

It is to be understood that both the foregoing general description and the following detailed descriptions are exemplary only, and are not restrictive of the invention.

BRIEF DESCRIPTION OF THE DRAWINGS

The accompanying drawings are included to provide a further understanding of the invention and are incorporated in and constitute a part of the specification. The drawings illustrate several embodiments of the invention and together with the description, serve to explain the principals of the invention. In the drawings.

A DESCRIPTION OF THE PREFERRED EMBODIMENTS

Reference will now be made in detail to the present preferred embodiments of the invention, examples of which are illustrated in the accompanying drawings.

An intravascular flow modifier (IFM) for use in a vessel according to the present invention comprises an outer layer formed of a strand. The strand is configured as a longitudinally oriented coil of adjacent helical loops extending between a first end and a second end of the outer layer.

Figure 1:
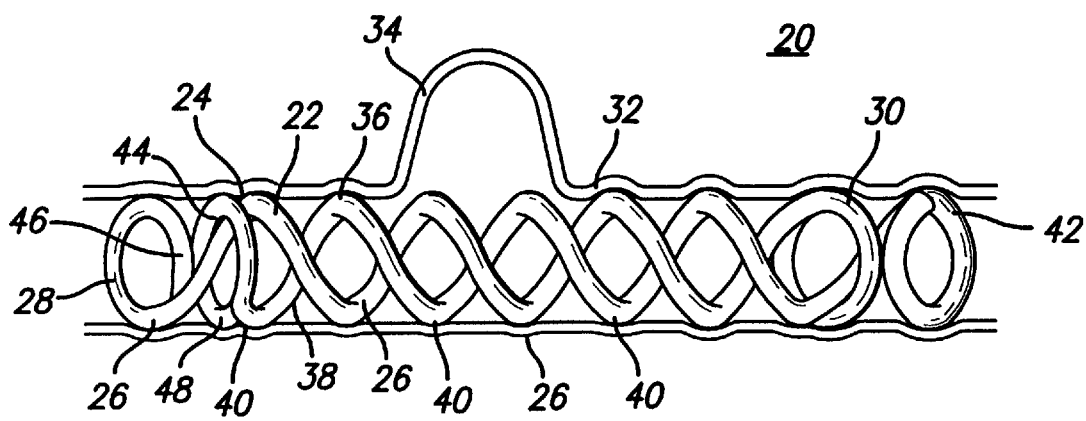
FIG. 1 is a perspective view of an IFM deployed in a cutaway of a vessel according to one embodiment.

An exemplary embodiment of the IFM of the present invention is shown deployed in a vessel in FIG. 1 and designated generally by reference numeral 20. The shaded segment of IFM is facing the inside of the loop and in this embodiment the outer layer has a beta helix and the inner layer has an alpha helix.

As broadly embodied herein, and referring to FIG. 1, an IFM 20 has an outer layer 22 formed of a strand. The strand is configured as a longitudinally oriented coil 24 of adjacent helical loops 26 extending between a first end 28 and a second end 30 of the outer layer 22. The outer layer 22 is secured in the vessel 32 by at least some of the helical loops 26 pressing against a portion of the interior surface of the vessel 32. The IFM 20 is typically deployed to alter flow dynamics and/or to keep an embolus deployed in a wide neck aneurysm in the aneurysm. The IFM 20 may also perform as a typical stent deployed to reinforce or strengthen a weakened or otherwise defective vessel. The vessel 32 is depicted with a defect 34, which is a wide neck aneurysm. While the IFM of the present invention is shown in use in the attached figures spanning an aneurysm, it is contemplated and within the scope of the claimed invention to deploy the IFM in any vessel of the body without regard to any particular defect.

The IFM 20 of the invention also includes an inner layer 36 formed of a strand. The strand is configured as a longitudinally oriented coil 38 of adjacent helical loops 40 extending between a first end 42 and a second end 44 of the inner layer 36. At least a portion of the outer layer 22 surrounds at least a portion of the inner layer 36 so that at least some of the loops 26 of the outer layer 22 overlap and contact at least some of the loops 40 of the inner layer 36. The helical loops 40 of the inner layer 36 preferably urge against the loops 26 of the outer layer 22 at crossing points.

Figure 2:
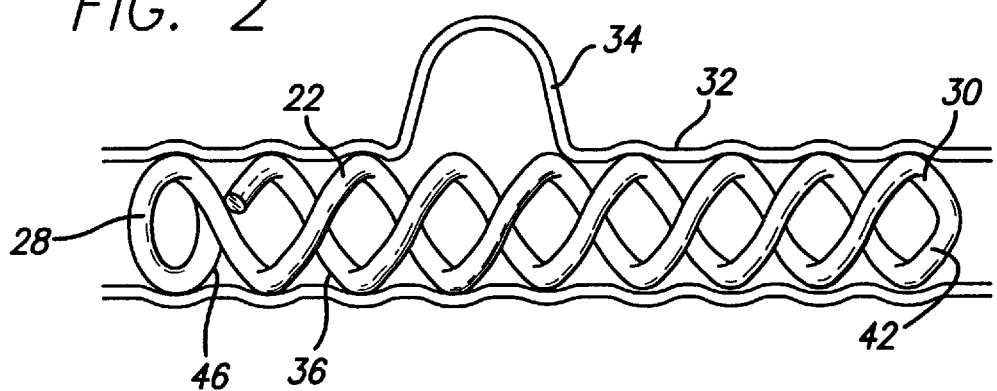
FIG. 2 is a perspective view of an IFM deployed in a cutaway of a vessel according to another embodiment.

As broadly embodied in FIG. 2, the preferred strand of the outer layer 22 and the inner layer 36 is a continuous strand, which is more preferably formed of or coated by a biocompatible material. Preferably, the strands of the outer and inner layers 22, 36 are formed of a high shape memory alloy, such as Nitinol alloy. An alloy such as Nitinol is plastically deformable at one temperature and can completely recover to their original shape on being raised to a higher temperature. Nickel-titanium alloys commonly referred to as nitinol are well known to those skilled in the art. The strand of the outer layer 22 and the strand of the inner layer 36 preferably have a circular, oval, rectangle, or triangular cross-section.

Use of the term "wire" within this application is not intended to limit the claimed invention to metal thread or the like. While metal is a preferred material, it is also contemplated that plastics, ceramics, glasses, and various compositions of materials could work within the scope of the claimed invention. Further, the term "strand" is not intended to limit the claimed invention to fibers or filaments twisted together to form a rope or braided line. While filaments could braided together to provide the strand of the claimed invention, the term "strand" is used herein to define multiple filaments working together whether braided together or not, as well as to define a single filament or line of material.

The preferred strand is a single line filament. The particular strand may be selected based on the strength, the memory, and the diameter needed for the IFM. The diameter of the strand is also a factor when the strand may pass over a perforating vessel that should not be blocked. In this case, the diameter is preferably small enough that even if a crossing point between the outer and inner layers is over a perforating vessel, complete blockage does not occur.

Figure 3:
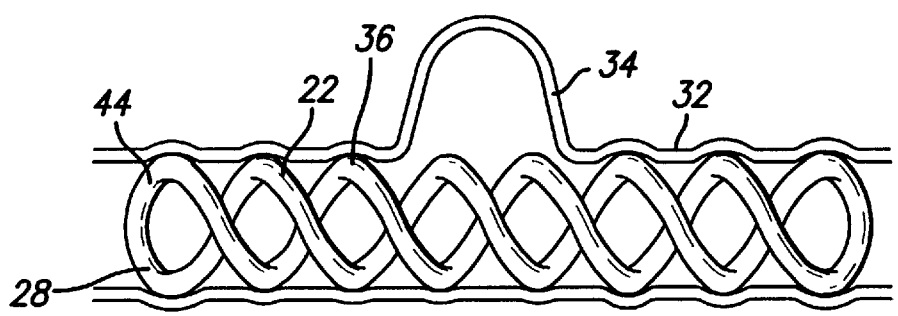
FIG. 3 is a perspective view of an IFM deployed in a cutaway of a vessel according to yet another embodiment.

In the embodiment of the IFM 20 shown in FIG. 1, the second end 30 of the outer layer 22 is anchored proximal to the first end 42 of the inner layer 36. As shown in the embodiment of FIG. 2, the second end 30 of the outer layer 22 preferably joins the first end 42 of the inner layer 36. In another embodiment of the IFM, and referring to FIG. 3, the first end 28 of the outer layer 22 attaches to the second end 44 of the inner layer 36 so that the continuous strand forms a loop. In the embodiment depicted in FIG. 3, the outer and inner layers 22, 36 are simultaneously deployed as the loop is released from the catheter.

As shown in the embodiment of FIG. 1, the first end 28 of the outer layer 22 may include means for inhibiting the wire strand from penetrating through the interior surface of the vessel 32, such as a loop 46 provided on the first end 28 of the wire strand The second end 44 of the inner layer 36 may include means for inhibiting the wire strand from penetrating through the interior surface of the vessel 32, such as a loop 48 on the second end 44 of the wire strand. Loops may be added to any exposed ends of the IFM 20. The first end 28 of the outer layer 22 and the second end 44 of the inner layer 36 are preferably distal ends relative to an insertion point into the vessel 32. The second end 30 of the outer layer 22 and the first end 42 of the inner layer 36 are preferably proximal ends relative to an insertion point into the vessel 32. Alternatively, the respective ends of the outer and inner layers 22, 36 may be reversed relative to the insertion point into the vessel 32 depending upon the method used to deploy the IFM.

The preferred helical loops 26, 40 of the outer and inner layers 22, 36 respectively are substantially circular. Both the helical loops 26, 40 of the outer and inner layers 22, 36 respectively wind in a predetermined direction. Preferably, the rotation of the helical loops 26, 40 of the outer and inner layers 22, 36 is in the same direction but with the helical loops 26 of the outer layer 22 having a alpha helix and the helical loops 40 of the inner layer 36 having a beta helix. Of course, the outer layer 22 may have the beta helix and the inner layer 36 may have the alpha helix. Preferably, the number of helical loops 26 of the outer layer 22 is N, where N is at least two, and the number of the helical loops 40 of the inner layer 36 is M, where M is at least two.

Figure 4A:
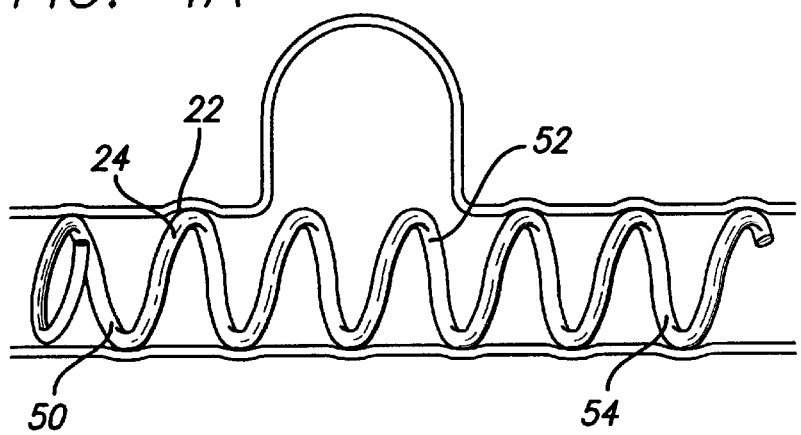
FIG. 4A is a perspective view of the outer layer of an IFM deployed in a cutaway of a vessel according to one embodiment.
Figure 4B:
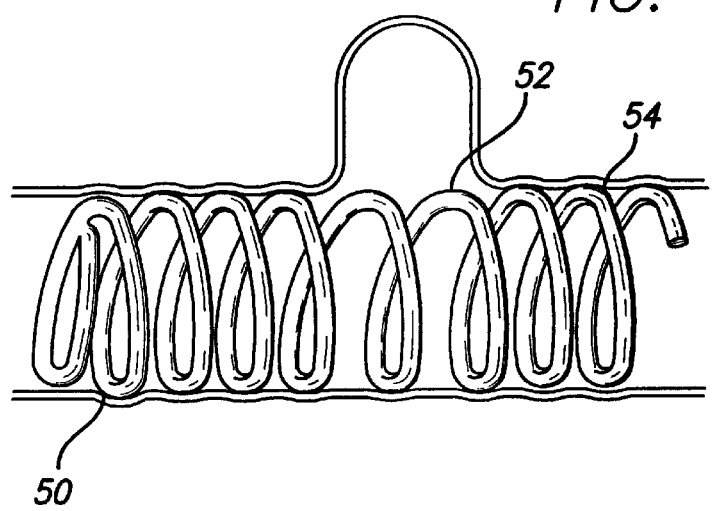
FIG. 4B is a perspective view of the outer layer of an IFM deployed in a cutaway of a vessel according to another embodiment of the invention.

In another embodiment of the invention broadly depicted in FIG. 4A, the outer layer 22 is divided into at least a first end portion 50, a middle portion 52, and a second end portion 54 along the longitudinally oriented coil 24. The pitch of the middle portion 52 may be smaller than the pitch of the first end and second end portions 50, 54. Alternatively, as shown in FIG. 4B, the pitch of the middle portion 52 may be larger than the pitch of the first end and second end portions 50, 52. The pitch of the first and second end portions 50, 54 preferably provides a gap between the helical loops of between 3 and 7 mm, while the pitch of the middle portion 52 provides a gap between the helical loops 26 of between 0.5 and 3 mm.

Figure 5:
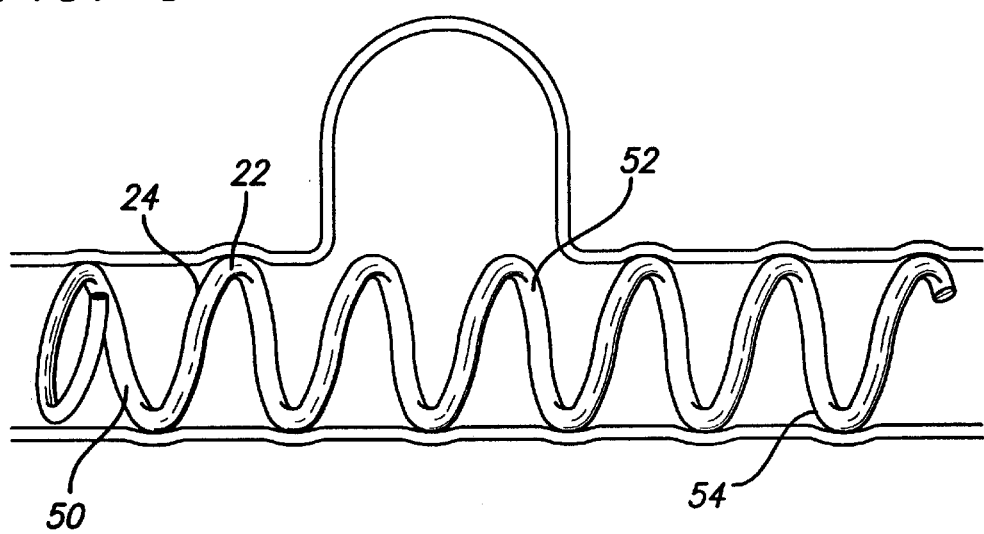
FIG. 5 is a perspective view of the outer layer of an IFM deployed in a cutaway of a vessel according to yet another embodiment.

As shown in FIG. 5, the diameter of the wire strand of the first end and second end portions 50, 54 of the outer layer 22 may be smaller than the diameter of the wire strand of the middle portion 52. A preferred diameter of the wire strand of the outer layer 22 is no greater than 0.020 inches. A more preferred diameter of the wire strand of the outer layer 22 is between 0.00025 and 0.006 inches. The diameter of the wire strand of the outer layer 22 comprising the first end and second end portions 50, 54 is more preferably between 0.001 and 0.002 inches, and the diameter of the wire strand comprising the middle portion 52 is more preferably between 0.003 and 0.004 inches.

Figure 6A:
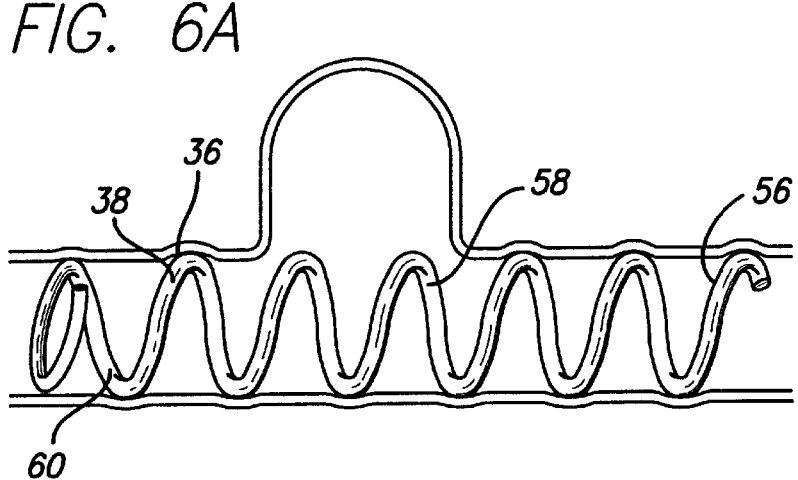
FIG. 6A is a perspective view of the inner layer of an IFM deployed in a cutaway of a vessel according to one embodiment.
Figure 6B:
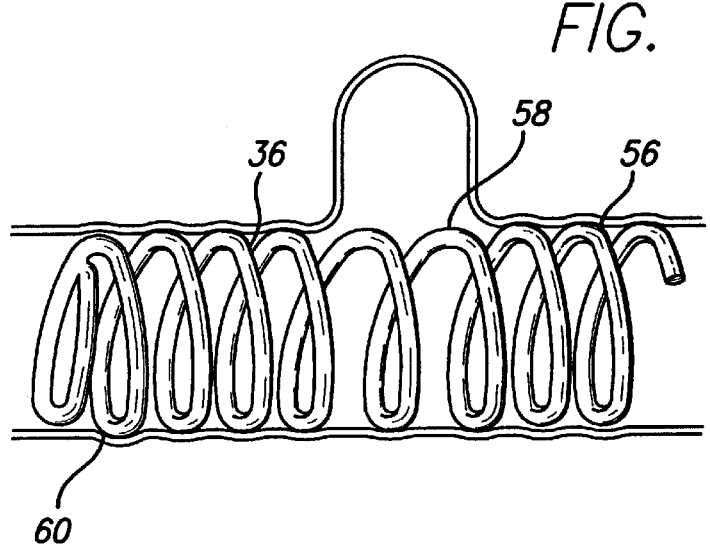
FIG. 6B is a perspective view of the inner layer of an IFM deployed in a cutaway of a vessel according to another embodiment of the invention.

As with the outer layer 22, and as shown in FIG. 6A, the inner layer 36 may be divided into at least a first end portion 56, a middle portion 58, and a second end portion 60 along the longitudinally oriented coil 38. The pitch of the middle portion 58 may be smaller than the pitch of the first end and second end portions 56, 60. Alternatively, and referring to FIG. 6B, the pitch of the middle portion 58 may be larger than the pitch of the first end and second end portions 56, 60. The pitch of the first and second end portions 56, 60 preferably provides a gap between the helical loops 40 of between 3 and 7 mm, while the pitch of the middle portion 58 provides a gap between the helical loops 40 of between 0.5 and 3 mm.

Figure 7:
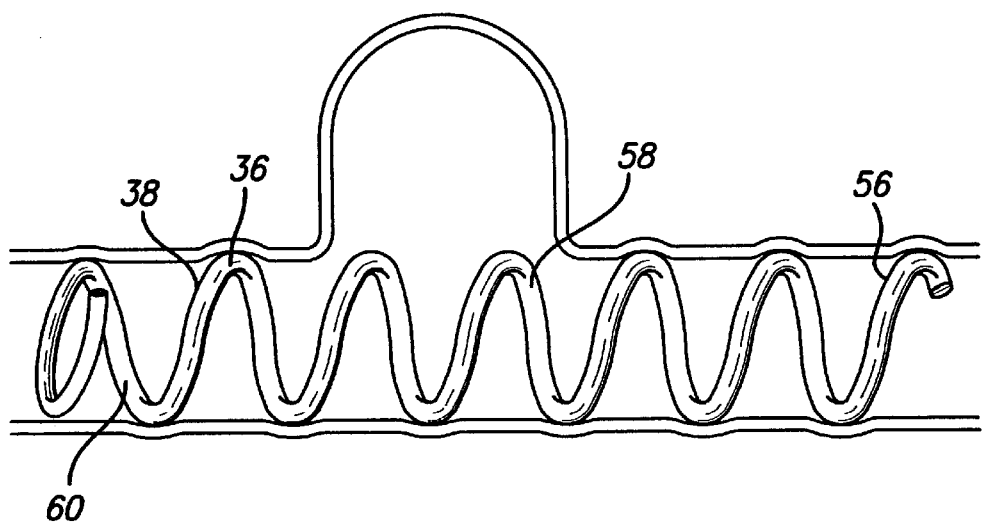
FIG. 7 is a perspective view of the inner layer of an IFM deployed in a cutaway of a vessel according to yet another embodiment.

As shown in FIG. 7, the diameter of the wire strand of the first end and second end portions 56, 60 of the inner layer 36 may be smaller than the diameter of the wire strand of the middle portion 58. A preferred diameter of the wire strand of the inner layer 36 is no greater than 0.020 inches. A more preferred diameter of the wire strand of the inner layer 36 is between 0.00025 and 0.006 inches. The diameter of the wire strand of the inner layer 36 comprising the first end and second end portions 56, 60 is more preferably between 0.001 and 0.002 inches, and the diameter of the wire strand comprising the middle portion 58 is more preferably between 0.003 and 0.004 inches. The helical loops 40 of the inner layer 36 preferably have a substantially constant inner diameter.

A preferred use for IFM 20 of the present invention is for bridging a defect in a cranial vessel. For intracranial use the wire strand of the outer and inner layers 22, 36 is preferably a continuous strand to minimize the number of exposed ends and potential of puncturing the vessel. The strand is preferably formed of a high shape memory alloy to readily permit the IFM 20 to be straightened, or at least have its coiled diameter reduced for insertion into the vessel, and then have it assume its deployed configuration when released from the delivering catheter. The preferred helical loops 26, 40 of the outer and inner layers 22, 36 are substantially circular. Additionally, the IFM 20 has an outside diameter, which is preferably between about 1.5 and 12 mm.

Figure 8:
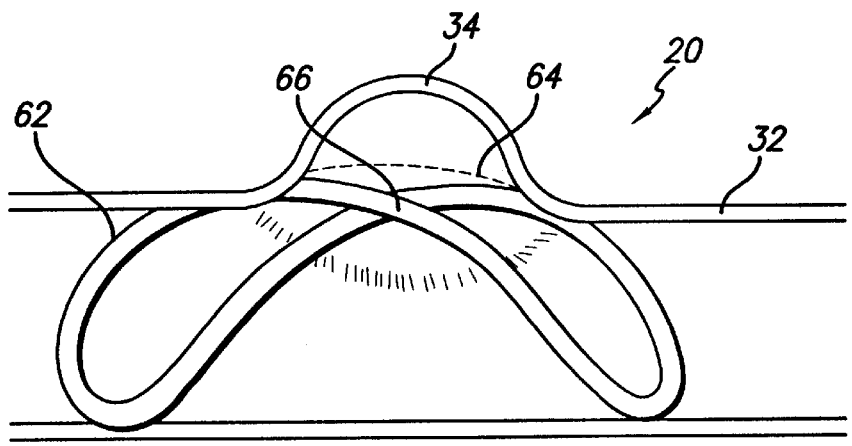
FIG. 8 is a perspective view of an IFM deployed in a cutaway of a vessel according to another embodiment.
Figure 9:
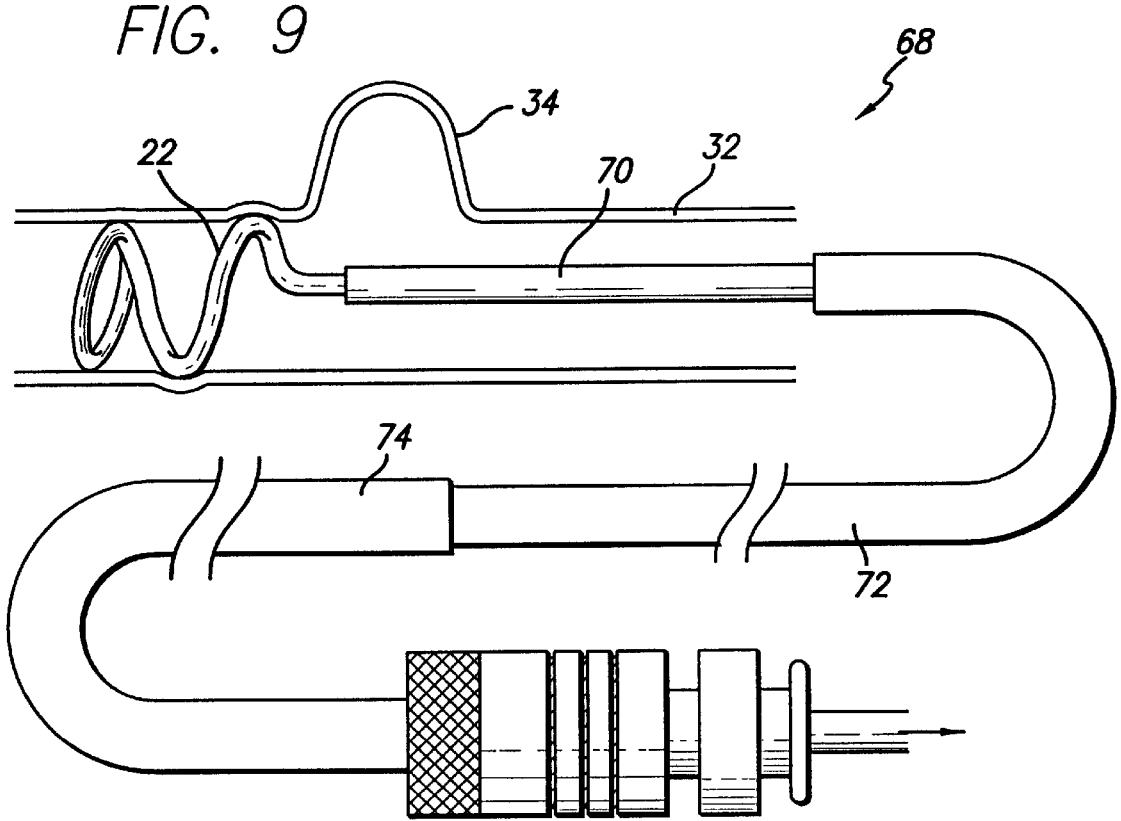
FIG. 9 is a side view of the assembly beginning deployment of a perspective view of the outer layer of an IFM in a cutaway of a vessel according to one embodiment.
Figure 10:
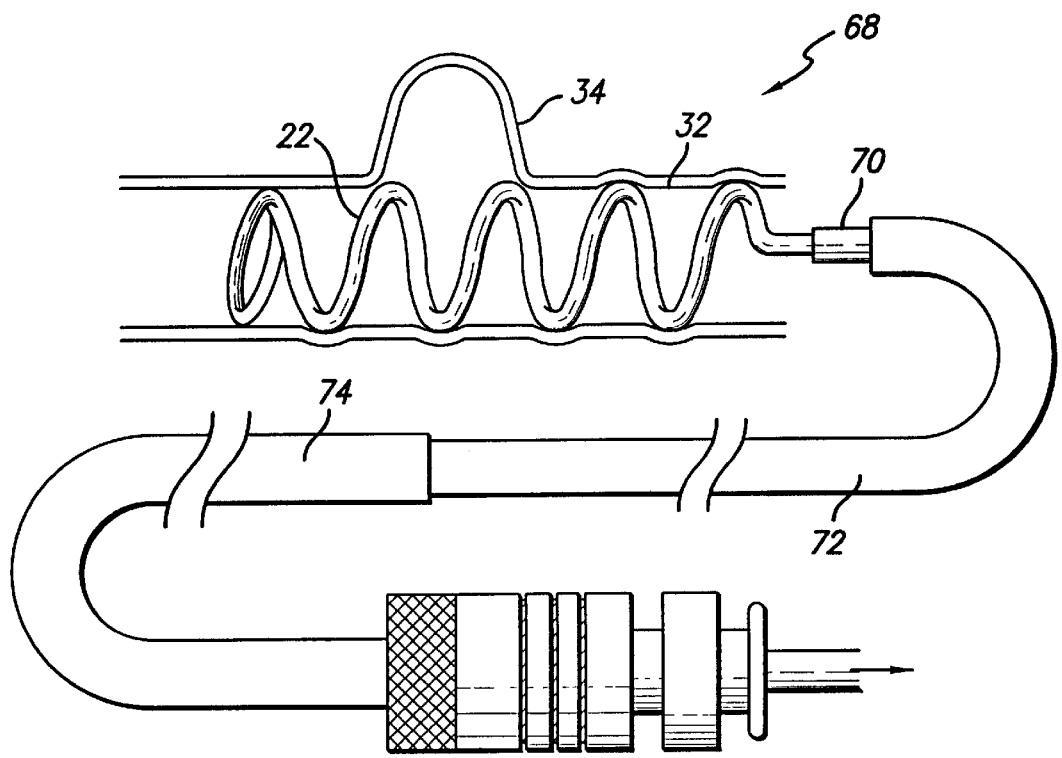
FIG. 10 is a side view of the assembly completing deployment of a perspective view of the outer layer of an IFM in a cutaway of a vessel according to the embodiment of FIG. 9.
Figure 11:
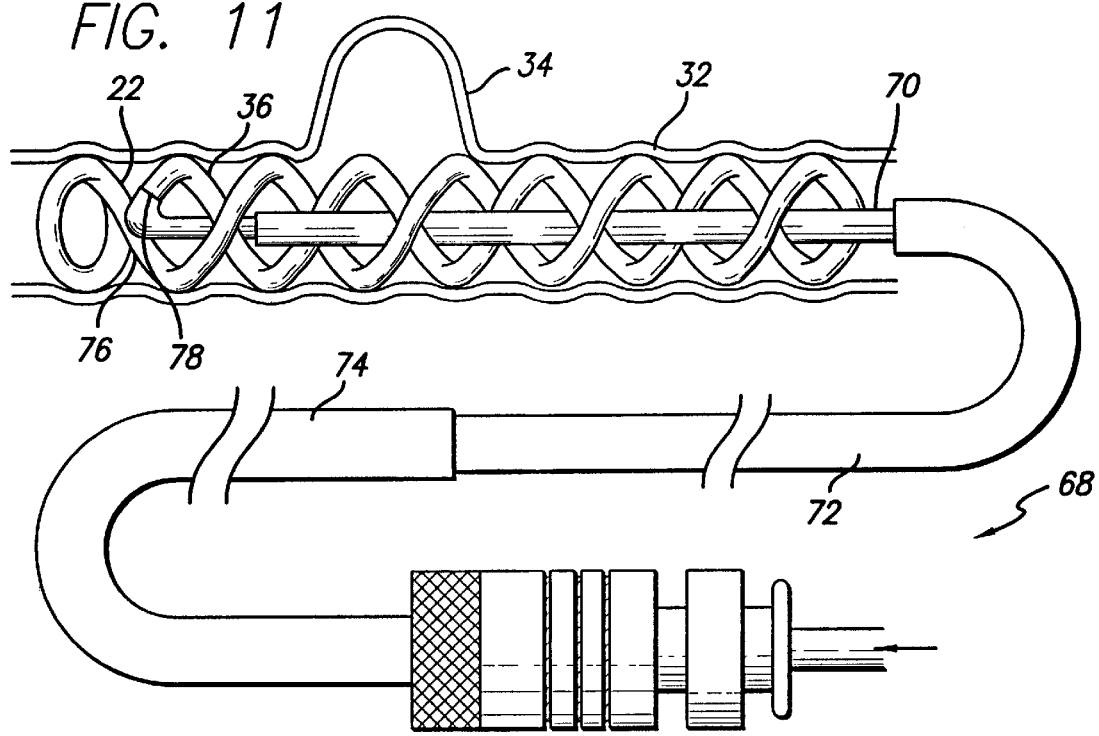
FIG. 11 is a side view of the assembly completing deployment of a perspective view of the inner layer of an IFM in a cutaway of a vessel according to the embodiment of FIG. 9.
Figure 12:
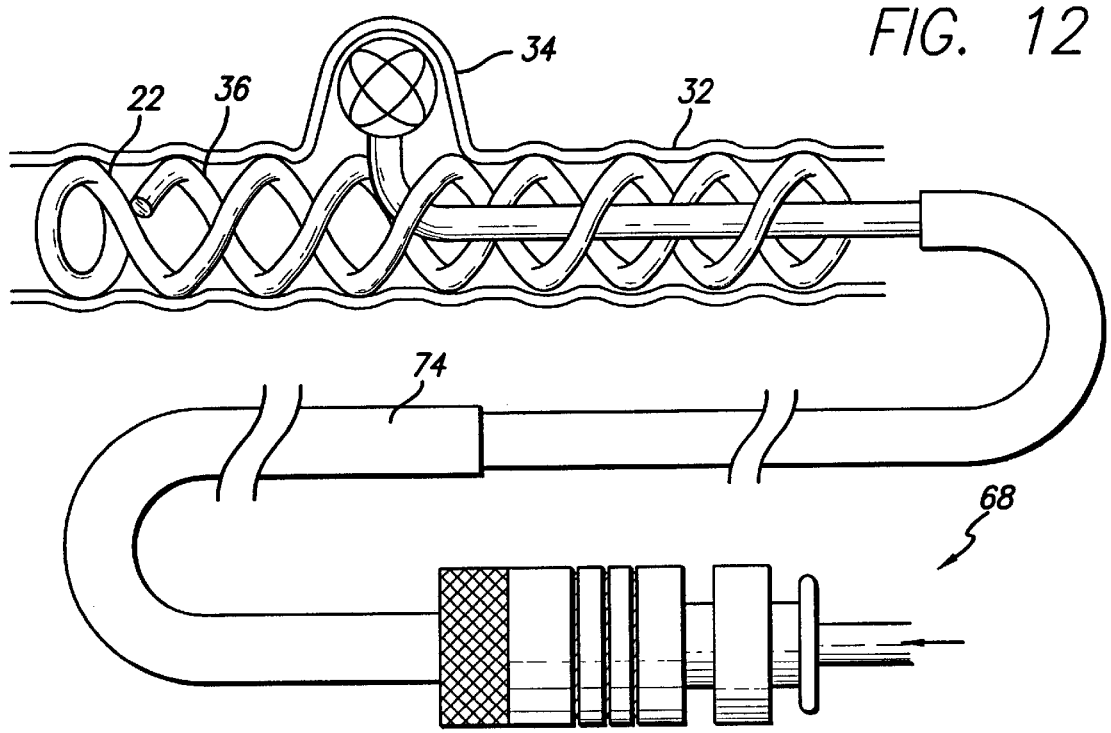
FIG. 12 is a side view of the assembly deploying a perspective view of a thrombogenic device in a cutaway of a vessel having a defect according to the embodiment of FIG. 9.

Yet another embodiment of the invention is broadly depicted in FIG. 8. The IFM 20 has at least one outer helical loop 62 formed of a strand of wire. The outer helical loop 62 is secured in the vessel 32 by at least some portion of the helical loop 62 pressing against a portion of the interior surface of the vessel 32. The IFM 20 also has at least one inner helical loop 64 formed of a strand of wire. At least some portion of the outer helical loop 62 surrounds at least a portion of the inner helical loop 64 so that at least some of the outer helical loop 62 overlaps and contacts at least some of the inner helical loop 64. Preferably, the outer helical loop 62 overlaps and contacts the inner helical loop 64 at a crossing point 66. More preferably, at least one crossing point 66 is adjacent to the defect 34 in the interior of the vessel 32. The IFM 20 of this embodiment may have an arched figure eight structure, and preferably has the crossing point 66 near the defect 34 of the vessel 32.

The invention also includes an assembly for an intravascular repair of a defect of a body vessel.

An exemplary embodiment of the assembly of the present invention is shown in FIGS. 9–12 and designated generally by the reference numeral 68.

As broadly embodied herein, and referring to FIGS. 9–12, an assembly 68 has an elongated first catheter 70 and an IFM 20 having a deployed configuration when in the vessel 32 at a site of the defect 34 and a pre-deployed configuration for movement through the first catheter 70. The IFM 20 includes an outer layer 22 and an inner layer 36 as discussed above. The first catheter 70 has a proximal end, a distal end, and a central lumen extending axially therethrough. The lumen has a size and shape complementary to the pre-deployed configuration of the IFM 20 such that the IFM 20 is axially slidable therethrough. A preferred first catheter 70 has an outside diameter of between about 0.010 and about 0.014 inches and an inside diameter of between about 0.004 and about 0.006 inches. The small diameter of the catheter permits access to vessels of the body previously not available for IFM deployment.

The assembly also includes a second catheter 72 having a distal end, a proximal end, and a central lumen extending axially therethrough. The lumen of the second catheter has a size and shape complementary to the first catheter 70 such that the first catheter 70 is axially slidable therein. At least a portion of the distal end of the first catheter 70 can be inserted into the lumen of the second catheter 72 at the proximal end and passes through the lumen of the second catheter 72 and exits the second catheter 72 at the distal end. A preferred second catheter 72 has an outside diameter of approximately 1 mm and an inside diameter of at least approximately 0.022 inches. The small diameter of the second catheter permits access to vessels of the body previously not available for IFM deployment utilizing a catheter-in-catheter assembly.

The assembly further has a third catheter 74 having a distal end, a proximal end, and a central lumen extending axially therethrough. The lumen of the third catheter 74 has a size and shape complementary to the second catheter 72 such that the second catheter 72 is axially slidable therein. At least a portion of the distal end of the second catheter 72 can be inserted into the lumen of the third catheter 74 at the proximal end and passes through the lumen of the third catheter 74 and exits the third catheter 74 at the distal end.

Finally, and referring to FIGS. 9–12, the present invention also includes a method of forming an IFM 20 at a pre-selected segment of a vessel 32. The method comprises the steps of moving the IFM 20 through a catheter 70 up to the pre-selected segment of the vessel 32; manipulating at least one of the outer layer 22 of wire strand and the catheter to deploy the outer layer 22 of strand in the pre-selected segment of vessel 32 as a longitudinally oriented coil 24 of adjacent helical loops 26; and manipulating at least one of the inner layer 36 of wire strand and the catheter 70 to deploy the inner layer of strand in the pre-selected segment of vessel as a longitudinally oriented coil 38 of adjacent helical loops 40 within the first portion of the IFM 20.

The step of moving preferably includes the step of insulating the IFM 20 within the catheter 70. When Nitinol metal or any other temperature reactive memory materials are used for the IFM 20, a user has reduced the IFM 20 diameter under conditions that cause the IFM 20 to expand towards its initial diameter when reaching a predetermined temperature. For example, an IFM could be formed as a coil, then straightened into a wire strand, then upon reaching a predetermined temperature in the body of a patient become a coil again. To keep the IFM from transforming into a coil before being placed in a pre-selected segment of a vessel, the IFM can be insulated from the body by the catheter either alone or in conjunction with cooling fluids and gases. Of course, the IFM could be formed of memory metal that does not transform at normal body temperatures or at any temperature.

Additionally, while memory metals are one preferred embodiment of the claimed invention, other IFM materials may be used in combination with an IFM delivery system that mechanically restrains the IFM in a reduced diameter pre-deployed configuration. A single catheter may have the structural properties to restrain a coiled IFM that has been elongated into a pre-deployed configuration. Further, the assemblies described herein can utilize the catheter-in-catheter arrangement to provide additional structural rigidity for mechanically restraining an IFM.

The method may also include the step of inserting the IFM 20 into the catheter 70 prior to the step of moving. Further, the method may include the step of elongating the IFM 20 prior to inserting the IFM 20 into the catheter 70. The step of elongating the IFM 20 preferably includes the step of straightening the IFM 20 to a substantially linear configuration.

The preferred catheter 70 may be referred to as a micro-catheter due to its relative size in the preferred use for deploying an intracranial IFM. While the relative sizes of the catheters are given in view of a preferred use for deploying an intracranial IFM, it is contemplated within the scope of the claimed invention that the assembly and method will be used in all vessels of the body.

The step of inserting may further include the step of providing an elongated guide catheter 72 having a size and shape complementary to the micro-catheter 70 such that the micro-catheter 70 is axially slidable therethrough. The guide catheter 72 is preferably positioned in the vessel 32 with the distal end of the guide catheter 72 being oriented near the pre-selected segment of the vessel 32. The method may further include the step of inserting at least a portion of the distal end of the micro-catheter 70 into the lumen of the guide catheter 72 at the proximal end and passing through the lumen of the guide catheter 72 and exiting the guide catheter 72 at the distal end prior to the step of moving the IFM.

The step of inserting preferably further comprises the step of providing an elongated angiographic catheter 74 having a size and shape complementary to the guide catheter 72 such that the guide catheter 72 is axially slidable therethrough. The angiographic catheter 74 is preferably positioned in the vessel 32 with the distal end of the angiographic catheter 74 oriented closer to an insertion point into the vessel 32 than the distal end of the guide catheter 72. The method preferably includes the step of inserting at least a portion of the distal end of the guide catheter 72 into the lumen of the angiographic catheter 74 at the proximal end. The guide catheter 72 passes through the lumen of the angiographic catheter 74 and exits the angiographic catheter 74 at the distal end prior to the step of moving the IFM 20.

A preferred method of practicing the invention includes the step of inserting the angiographic catheter 74 into the vessel 32 before inserting the guide catheter 72 containing the micro-catheter 70 into the vessel 32. The method preferably also includes the steps of halting the advancement of the angiographic catheter 74 into the vessel 32 and continuing to advance the guide catheter 72 and the micro-catheter 70 into the vessel 32. For deployment of an intracranial IFM, the angiographic catheter 74 is halted on the proximal side of the carotid artery. The angiographic catheter 74 is well known in the art and is only unique in its combination with the other elements of the assemble and method disclosed herein. Additionally, other known devices and methods, such as the use of guide wires in conjunction with catheters may be used with the disclosed assembly and method.

The method preferably also includes the steps of halting the advancement of the guide catheter 72 into the vessel 32 and continuing to advance the micro-catheter 70 into the vessel 32. For deployment of an intracranial IFM, the guide catheter 72 is preferably halted on the proximal side of the defect. The guide catheter 72 has a structural that permits it to navigate the carotid artery and other tiny vessels having tight turns.

In one embodiment of the method invention, the steps of manipulating include the steps of selectively varying the spacing between the adjacent helix loops 26, 40 of the outer and inner layers, 22, 36 respectively. For an intracranial IFM, the option of varying the spacing or controlling the pitch at various points alone the longitudinal coil is especially important. The physician can manipulate the relative movement of the IFM and micro-catheter 70 to stretch the coil out or bunch it up to avoid blocking perforating arteries. For example, if the deployed IFM blocks off a perforating artery, the brain tissue fed by the blocked artery will be starved of blood resulting in the death of surrounding brain cells. Further, the physician can tighten the coil by reducing the pitch to more fully obstruct the blood flow into the aneurysm.

The method may further include the step of expanding the IFM 20 substantially to a pre-elongated diameter during the steps of manipulating. The step of expanding the IFM 20 may includes the step of warming the wire strand of the outer layer 22 and the wire strand of the inner layer 36.

The step of manipulating at least one of the outer layer 22 and the catheter preferably includes the step of providing the outer layer 22 with a number of loops where the number is at least two. Alternatively, the step of manipulating at least one of the outer layer 22 and the catheter may include the step of providing the outer layer 22 with a single loop. The step of manipulating at least one of the inner layer 36 and the catheter preferably includes the step of providing the inner layer 36 with a number of loops where the number is at least two. Alternatively, the step of manipulating at least one of the inner layer 36 and the catheter 70 may include the step of providing the inner layer 36 with a single loop. In the embodiment including a single loop for the outer and inner layer 22, 36, the loops of the outer and inner layer 22, 36 may have their respective ends joined to one another in the configuration of a twisted loop, such as in a figure-eight design.

The step of manipulating the first portion of the IFM 20 includes the step of feeding the outer layer 22 out of the catheter 70 to produce the portions, pitch, winding, and gap criteria from the IFM discussion above according to the physicians desires. The step of manipulating the outer layer 22 or first portion of the IFM preferably includes the step of pushing the first portion out of the catheter 70 and into the pre-selected segment. More preferably, the step of pushing includes pushing the first portion out of the distal end of the catheter 70 while pulling the proximal end of the catheter 70 towards the insertion point into the vessel 32. The relative movement between the strand and the catheter 70 allows the physician to deploy an IFM specifically suited for repair of the defect in the vessel.

The step of deploying the second portion of the IFM 20 includes the step of producing the inner layer 36 with portions, pitch, winding, and gap criteria from the IFM discussion above. The step of manipulating the inner layer 36 or second portion of the IFM 20 preferably includes the step of pushing the second portion out of the catheter 70 and into the pre-selected segment. More preferably, the step of pushing includes pushing the second portion out of the distal end of the catheter 70 at a predetermined rate while pushing the distal end of the catheter 70 towards the pre-selected segment of the vessel 32 at a rate slower than the predetermined rate of the second portion.

Once the physician has completed weaving the second portion of the IFM within the first portion of the IFM, the strand may be cut in a number of ways. By way of example, and referring to FIG. 11, a ball 76 and claw 78 are depicted cutting the strand.

Alternatively, the strand may be cut by a controlled electric discharge from the catheter 70 to a reduced diameter portion of the strand. A preferred method uses a strand of a pre-selected length, thereby eliminating any need for a cutting step. Other devices and methods for cutting a strand of an IFM are known to those skilled in the art and may be readily adapted to the present invention.

A preferred method of practicing the present invention includes the steps of straightening the IFM 20 to a substantially linear configuration; inserting the angiographic catheter 74 into the vessel 32; inserting the micro-catheter 70 into the guide catheter 72, and the guide catheter 72 into the angiographic catheter 74; inserting the IFM 20 into the micro-catheter; positioning the distal end of the angiographic catheter 74 at a predetermined location in the vessel 32 proximal to the pre-selected segment of the vessel 32; advancing at least a portion of the distal end of the guide catheter 72 through the angiographic catheter 74 and exiting the angiographic catheter 74 at the distal end; positioning the guide catheter 72 in the vessel 32 with the distal end of the guide catheter 72 being oriented between the pre-selected segment of the vessel 32 and the distal end of the angiographic catheter 74; advancing at least a portion of the distal end of the micro-catheter 70 through the guide catheter 72 and exiting the guide catheter 72 at the distal end; moving the IFM 20 through the micro-catheter 70 up to the pre-selected segment of the vessel 32; manipulating at least one of the outer layer 22 of wire strand and the catheter 70 to deploy the outer layer 22 of strand in the pre-selected segment of vessel 32 as a longitudinally oriented coil 24 of adjacent helical loops 26; and manipulating at least one of the inner layer 36 of wire strand and the catheter 70 to deploy the inner layer 36 of strand in the pre-selected segment of vessel 32 as a longitudinally oriented coil 38 of adjacent helical loops 40.

Figure 13:
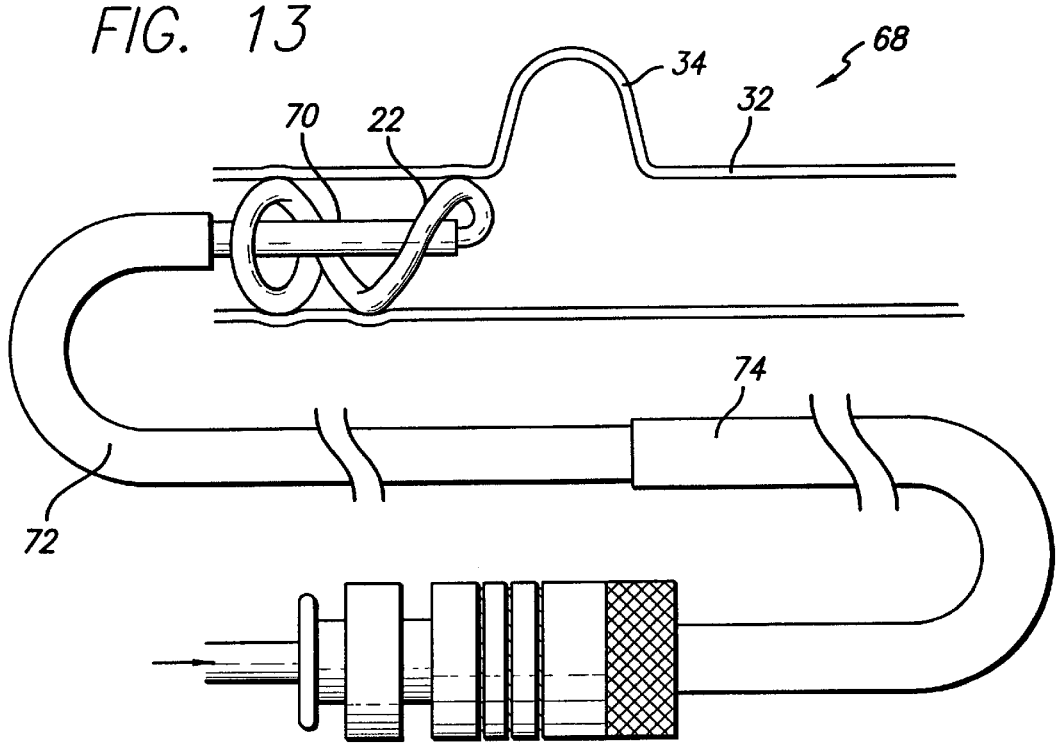
FIG. 13 is a side view of the assembly beginning deployment of a perspective view of the outer layer of an IFM in a cutaway a vessel according to another embodiment.
Figure 14:
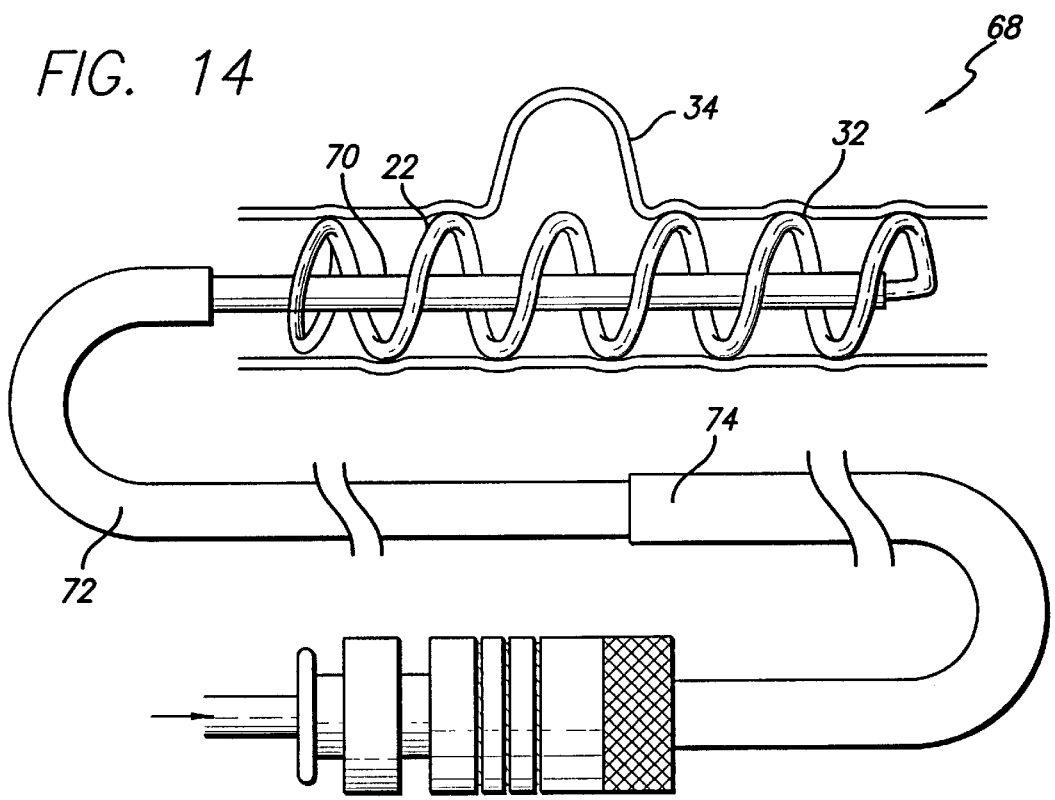
FIG. 14 is a side view of the assembly completing deployment of a perspective view of the outer layer of an IFM in a cutaway of a vessel according to the embodiment of FIG. 13.
Figure 15:
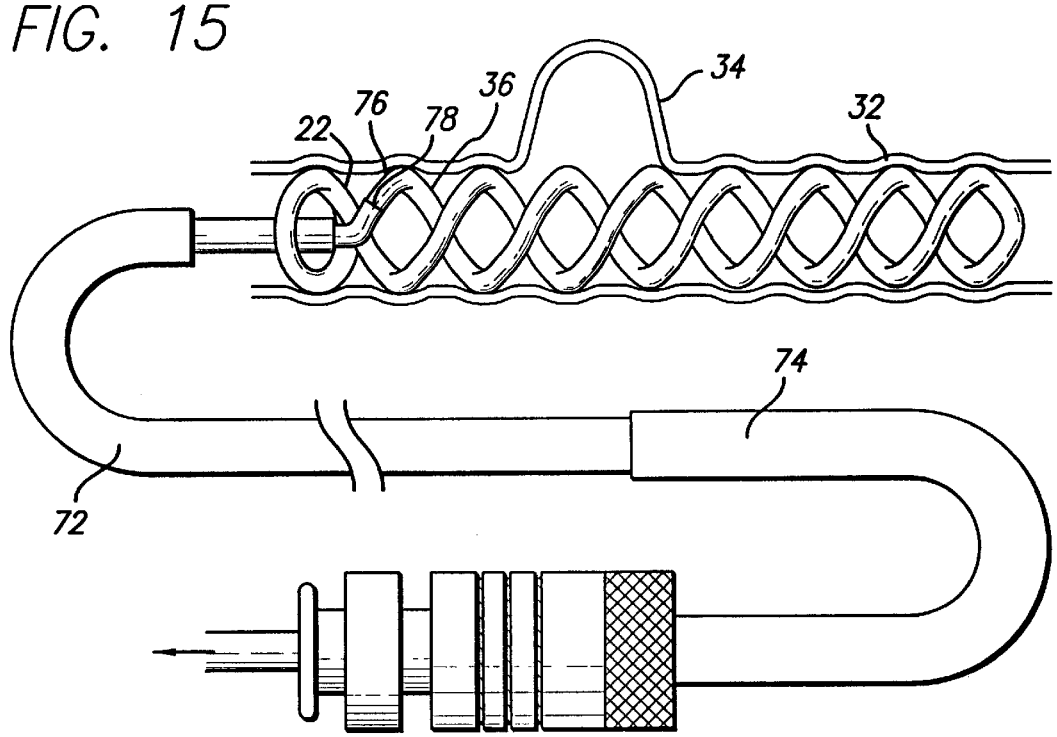
FIG. 15 is a side view of the assembly completing deployment of a perspective view of the inner layer of an IFM in a cutaway of a vessel according to the embodiment of FIG. 13.

Another embodiment of a method of forming an IFM 20 at a pre-selected segment of a vessel 32 is illustrated in FIGS. 13–15. This embodiment is similar to the embodiment discussed above except that the step of pushing the first portion includes pushing the first portion out of the distal end of the catheter 70 at a predetermined rate while pushing the catheter 70 towards the pre-selected segment of the vessel 32 at a rate slower than the predetermined rate of the first portion as shown in FIGS. 13 and 14, and the step of pushing the second portion includes pushing the second portion out of the distal end of the catheter 70 while pulling the catheter 70 towards the insertion point into the vessel 32. This embodiment of the method has the advantage of having catheter 70 already positioned on the distal side of the IFM upon completing the outer layer 22. Therefore, the catheter 70 need only be pulled toward the insertion point as strand is pushed out to form the inner layer 36. Thus, the catheter 70 cannot be pushed into the outer layer 22 during the step of manipulating to deploy the inner layer 36.

While the above method and techniques have been disclosed in connection with the preferred IFM having an outer layer and an inner layer, it is contemplated and within the scope of the claimed method that an IFM and/or stent having a single layer or coil may be deployed according to the claimed method. The method permits one to manipulate and control the final configuration of the IFM during deployment.

While there has been illustrated and described what is at present considered to be a preferred embodiment of the present invention, it will be understood by those skilled in the art that various changes and modifications may be made, and equivalents may be substituted for elements thereof, without departing from the true scope of the invention. Therefore, it is intended that this invention not be limited to the particular embodiments disclosed herein, but that the invention include all embodiments falling within the scope of the appended claims.

What is claimed is:

1. An intravascular flow modifier (IFM) for use in a vessel, the vessel having an interior surface, the IFM comprising:

an outer layer formed of a strand, said strand being formed of a shape memory material, said strand having a pre-deployed configuration that is substantially linear, and said strand having a deployed configuration of a longitudinally oriented coil of adjacent substantially circular helical loops extending between a first end and a second end of said outer layer, said outer layer adapted to be secured in the vessel in said deployed configuration by at least some of said helical loops pressing against a portion of the interior surface of the vessel; and an inner layer formed of a strand, said strand being formed of a shape memory material, said strand having a pre-deployed configuration that is substantially linear, and said strand having a deployed configuration of a longitudinally oriented coil of adjacent substantially circular helical loops extending between a first end and a second end of said inner layer, at least a portion of said outer layer surrounding at least a portion of said inner layer in said deployed configuration so that at least some of said loops of said outer layer overlap and contact at least some of said loops of said inner layer no more than twice for each of said loops, wherein said outer layer and said inner layer are connected to form a continuous strand, and wherein said first end of said outer layer is connected to said second end of said inner layer to form a loop.

2. The IFM of claim 1, wherein said continuous strand is made of a biocompatible material.

3. The IFM of claim 1, wherein said strands are made of a Nitinol alloy.

4. The IFM of claim 1, wherein said second end of said outer layer is adapted to be anchored to the vessel proximal to said first end of said inner layer.

5. The IFM of claim 1, wherein said second end of said outer layer is joined to said first end of said inner layer to form a loop.

6. The IFM of claim 1, wherein said first end of said outer layer includes means for inhibiting said strand from penetrating through the interior surface of the vessel.

7. The IFM of claim 6, wherein said inhibiting means includes a loop on said first end of said strand.

8. The IFM of claim 1, wherein said second end of said inner layer includes means for inhibiting said strand from penetrating through the interior surface of the vessel.

9. The IFM of claim 8, wherein said inhibiting means includes a loop on said second end of said strand.

10. The IFM of claim 1, wherein said first end of said outer layer and said second end of said inner layer are distal ends relative to an insertion point into the vessel.

11. The IFM of claim 1, wherein said second end of said outer layer and said first end of said inner layer are proximal ends relative to an insertion point into the vessel.

12. The IFM of claim 1, wherein both said helical loops of said outer and inner layers wind in a predetermined direction.

13. The IFM of claim 1, wherein the number of said helical loops of said outer layer is N, where N is at least two.

14. The IFM of claim 1, wherein the number of said helical loops of said inner layer is M, where M is at least two.

15. The IFM of claim 1, wherein said outer layer deployed configuration is divided into at least a first end portion, a middle portion, and a second end portion along said longitudinally oriented coil, said first end, middle, and second end portions each having a pitch, the pitch of said middle portion being smaller than the pitch of said first end and second end portions.

16. The IFM of claim 15, wherein the pitch of said first end portion provides a gap between said helical loops of between 3 an 7 mm, the pitch of said middle portion provides a gap between said helical loops of between 0.5 and 3 mm, and the pitch of said second end portion provides a gap between said helical loops of between 3 and 7 mm.

17. The IFM of claim 15, wherein said strand of said outer layer has a diameter, the diameter of said strand of said first end and second end portions is smaller than the diameter of said strand of said middle portion.

18. The IFM of claim 17, wherein the diameter of said strand of said outer layer is no greater than 0.020 inches.

19. The IFM of claim 18, wherein the diameter of said strand of said outer layer comprising said first end and second end portions is between 0.001 and 0.002 inches, and the diameter of said strand comprising said middle portion is between 0.003 and 0.004 inches.

20. The IFM of claim 1, wherein said outer layer deployed configuration is divided into a first end portion, a middle portion, and a second end portion along said longitudinally oriented coil, said first end, middle, and second end portions each having a pitch, the pitch of said middle portion being larger than the pitch of said first end and second end portions.

21. The IFM of claim 1, wherein said inner layer deployed configuration is divided into at least a first end portion, a middle portion, and a second end portion along said longitudinally oriented coil, said first end, middle, and second end portions each having a pitch, the pitch of said middle portion being smaller than the pitch of said first end and second end portions.

22. The IFM of claim 21, wherein the pitch of said first end portion provides a gap between said helical loops of between 3 and 7 mm, the pitch of said middle portion provides a gap between said helical loops of between 0.5 and 3 mm, and the pitch of said second end portion provides a gap between said helical loops of between 3 and 7 mm.

23. The IFM of claim 21, wherein said strand of said inner layer has a diameter, the diameter of said strand of said first end and second end portions is smaller than the diameter of said strand of said middle portion.

24. The IFM of claim 23, wherein the diameter of said strand of said inner layer is no greater than 0.020 inches.

25. The IFM of claim 24, wherein the diameter of said strand of said inner layer comprising said first end and second end portions is between 0.001 and 0.002 inches, and the diameter of said strand comprising said middle portion is between 0.003 and 0.004 inches.

26. The IFM of claim 21, wherein said helical loops of said inner layer have a substantially constant inner diameter.

27. The IFM of claim 1, wherein said inner layer is divided into a first end portion, a middle portion, and a second end portion along said longitudinally oriented coil, said first end, middle, and second end portions each having a pitch, said pitch of said middle portion being larger than the pitch of said first end and second end portions.

28. An intravascular flow modifier (IFM) for use in a vessel, the vessel having an interior surface, the IFM comprising:

a continuous length of strand having a pre-deployed substantially linear configuration and a deployed configuration formed as a longitudinally oriented coil surrounding another longitudinally oriented coil, said coils forming an outer layer of adjacent substantially circular helical loops, said outer layer adapted to urge against a portion of the interior surface of the vessel, said helical loops of said inner layer urging against said loops of said outer layer at crossing points, no more than twice for each of said loops, said continuous length of strand forming at least one end loop.

29. An intravascular flow modifier (IFM) for use in a vessel, the vessel having an interior surface, the IFM comprising:

an outer layer formed of a strand having a first end, a second end opposite said first end, and having a pre-deployed configuration that is substantially linear and a deployed configuration in the form of a longitudinally oriented coil of adjacent helical loops between said first and second ends, said outer layer adapted to be secured in the vessel in said deployed configuration by at least some of said helical loops pressing against a portion of the interior surface of the vessel;

an inner layer formed of a strand having a first end, a second end opposite said first end, and having a pre-deployed configuration that is substantially linear and a deployed configuration in the form of a longitudinally oriented coil of adjacent loops between said first and second ends, at least a portion of said outer layer in its deployed configuration surrounding at least a portion of said inner layer in its deployed configuration so that at least some of said loops of said outer layer overlap and contact at least some of said loops of said inner layer no more than twice for each of said loops, said strand of said outer and inner layers being a continuous strand formed of a high shape memory alloy, said helical loops of said outer and inner layers being substantially circular in said respective deployed configurations, said second end of said outer layer joining said first end of said inner layer to form a loop, said first end of said outer layer and said second end of said inner layer being distal ends relative to an insertion point into the vessel, said second end of said outer layer and said first end of said inner layer being proximal ends relative to an insertion point into the vessel, said helical loops of said outer and inner layers winding in a predetermined direction.

30. An intracranial intravascular flow modifier (IFM) for use in a cranial vessel, the vessel having an interior surface, the IFM comprising:

an outer layer formed of a strand having a first end, a second end opposite said first end, and having a pre-deployed configuration that is substantially linear and a deployed configuration in the form of a longitudinally oriented coil of adjacent helical loops between said first and second ends, said outer layer adapted to be secured in the vessel in said deployed configuration by at least some of said helical loops pressing against a portion of the interior surface of the vessel;

an inner layer formed of a strand having a first end, a second end opposite said first end, and having a pre-deployed configuration that is substantially linear and a deployed configuration in the form of a longitudinally oriented coil of adjacent helical loops between said first and second ends, at least a portion of said outer layer in its deployed configuration surrounding at least a portion of said inner layer in its deployed configuration so that at least some of said loops of said outer layer overlap and contact at least some of said loops of said inner layer no more than twice for each of said loops, said strand of said outer and inner layers being a continuous strand formed of a high shape memory alloy, said helical loops of said outer and inner layers being substantially circular in said respective deployed configurations, said second end of said outer layer joining said first end of said inner layer to form a loop, said first end of said outer layer and second end of said inner layer being distal ends relative to an insertion point into the vessel, said second end of said outer layer and first end of said inner layer being proximal ends relative to an insertion point into the vessel, said IFM having an outside diameter of between about 1.5 and 12 mm.

31. The IFM of claim 30, wherein in said deployed configuration said outer layer is divided into a first end portion, a middle portion, and a second end portion along said longitudinally oriented coil, said first end, middle, and second end portions each having a pitch, the pitch of said middle portion being smaller than the pitch of said first end and second end portions, and said inner layer is divided into a first end portion, a middle portion, and a second end portion along the longitudinally oriented coil, said first end, middle, and second end portions each having a pitch, the pitch of said middle portion being smaller than the pitch of said first end and second end portions.

32. An assembly for an intravascular repair of a defect of a body vessel, the vessel having an interior surface, the assembly comprising:

an elongated first catheter;

an intravascular flow modifier (IFM) having a deployed configuration when in the vessel at a site of the defect and a pre-deployed substantially linear configuration for movement through said first catheter;

said IFM in said deployed configuration including an outer layer formed of a strand, said strand being configured as a longitudinally oriented coil of adjacent substantially circular helical loops extending between a first end and a second end of said outer layer, once deployed said outer layer adapted to be secured in the vessel by at least some of said loops urging against a portion of the interior surface of the vessel, and an inner layer formed of a strand, said strand being configured as a longitudinally oriented coil of adjacent substantially circular helical loops extending between a first end and a second end of said inner layer, once deployed in the vessel at the site of the defect at least a portion of said outer layer surrounding at least a portion of said inner layer so that at least some of said loops of said outer layer overlap and contact at least some of said loops of said inner layer no more than twice for each of said loops, wherein said outer layer and said inner layer are connected to form a continuous strand, and wherein said first end of said outer layer is connected to said second end of said inner layer to form a loop; and said first catheter having a proximal end, a distal end, and a central lumen extending axially therethrough, said lumen having a size and shape complementary to the pre-deployed configuration of said IFM such that said IFM is axially slidable therethrough.

33. The assembly of claim 32, further comprising a second catheter having a distal end, a proximal end, and a central lumen extending axially therethrough, said lumen of said second catheter having a size and shape complementary to said first catheter such that said first catheter is axially slidable therein, and such that at least a portion of said distal end of said first catheter can be inserted into said lumen of said second catheter at said proximal end and passes through said lumen of said second catheter and exits said second catheter at said distal end.

34. The assembly of claim 33, further comprising a third catheter having a distal end, a proximal end, and a central lumen extending axially therethrough, said lumen of said third catheter having a size and shape complementary to said second catheter such that said second catheter is axially slidable therein, and such that at least a portion of said distal end of said second catheter can be inserted into said lumen of said third catheter at said proximal end and passes through said lumen of said third catheter and exits said third catheter at said distal end.

35. The assembly of claim 33, wherein said second catheter has an inside diameter of at least approximately 0.022 inches.

36. The assembly of claim 32, wherein the vessel is a cranial vessel, and said IFM has a deployed diameter of between about 1.5 and 12 mm.

37. The assembly of claim 32, wherein said strand of said outer and inner layers has a diameter of no greater than about 0.020 inches.

38. The assembly of claim 32, wherein said first catheter has a outside diameter of between about 0.010 and about 0.014 inches.

39. The assembly of claim 32, wherein said first catheter has an inside diameter of between about 0.004 and about 0.006 inches.

40. The assembly of claim 33, wherein said second catheter has an outside diameter of approximately 1 mm.

41. An assembly for an intravascular repair of a defect of a body vessel, the vessel having an interior surface, the assembly comprising:

an intravascular flow modifier (IFM) having a deployed configuration when in the vessel at a site of the defect and a pre-deployed substantially linear configuration for movement through the vessel towards the site of the defect;

said IFM in said deployed configuration including an outer layer formed of a strand, said strand being configured as alongitudinally oriented coil of adjacent substantially circular helical loops extending between a first end and a second end of said outer layer, once deployed said outer layer adapted to be secured in the vessel by at least some of said loops urging against a portion of the interior surface of the vessel, and an inner layer formed of a strand, said strand being configured as a longitudinally oriented coil of adjacent substantially circular helical loops extending between a first end and a second end of said inner layer, once deployed in the vessel at the site of the defect at least a portion of said outer layer surrounding at least a portion of said inner layer so that at least some of said loops of said outer layer overlap and contact at least some of said loops of said inner layer no more than twice for each of said loops, wherein said outer layer and said inner layer are connected to form a continuous strand, and wherein said first end of said outer layer is connected to said second end of said inner layer to form a loop; and a means for moving and maintaining said IFM when in the pre-deployed configuration, the outer and inner layers of said IFM taking the deployed configuration when the moving and maintaining means is no longer applied thereto.

42. The IFM of claim 41, wherein the moving and maintaining means comprises an elongated first catheter having a proximal end, a distal end, and a central lumen extending axially therethrough, said lumen having a size and shape complementary to the respective size and shape of said IFM when in the pre-deployed configuration such that said outer and inner layers are axially slidable therein.

43. The IFM of claim 41, further comprising means for disposing said IFM within the vessel.

44. The IFM of claim 43, wherein the disposing means comprises:

an elongated first catheter having a proximal end, a distal end, and a central lumen extending axially therethrough, said lumen having a size and shape complementary to the respective size and shape of said IFM when in the pre-deployed configuration such that said IFM is axially slidable therein; and an elongated second catheter having a proximal end, a distal end, and a central lumen extending axially therethrough, said lumen having a size and shape complementary to said first catheter such that said first catheter is axially slidable therein, and such that at least a portion of said distal end of said first catheter can be inserted into said lumen of said second catheter at said proximal end and passes through said lumen of said second catheter and exits said second catheter at said distal end.

45. The IFM of claim 41, and further comprising means for selectively varying the gap between said adjacent helical loops of said outer and inner layers.

46. The IFM of claim 45, wherein said selectively varying means comprises:

an elongated first catheter having a proximal end, a distal end, and a central lumen extending axially therethrough, said lumen having a size and shape complementary to the respective size and shape of said IFM when in the pre-deployed configuration such that said IFM is axially slidable therein;

an elongated second catheter having a proximal end, a distal end, and a central lumen extending axially therethrough, said lumen having a size and shape complementary to said first catheter such that said first catheter is axially slidable therein, and such that at least a portion of said distal end of said first catheter can be inserted into said lumen of said second catheter at said proximal end and passes through said lumen of said second catheter and exits said second catheter at said distal end; and means for controlling axial movement of said IFM when in the pre-deployed configuration through said first catheter and out of said distal end of said first catheter.

47. The IFM of claim 46, wherein said controlling means includes means for controlling the axial movement of said IFM and said first catheter.

48. An assembly for an intravascular repair of a defect of a cranial vessel, the vessel having an interior surface, the assembly comprising:

an elongated first catheter;

an intravascular flow modifier (IFM) having a deployed configuration when in the vessel at a site of the defect and a pre-deployed substantially linear configuration for movement through said first catheter;

said IFM in said deployed configuration including an outer layer formed of a strand, said strand being configured as a longitudinally oriented coil of adjacent substantially circular helical loops extending between a first end and a second end of said outer layer, once deployed said outer layer adapted to be secured in the vessel by at least some of said loops urging against a portion of the interior surface of the vessel, and an inner layer formed of a strand, said strand being configured as a longitudinally oriented coil of adjacent substantially circular helical loops extending between a first end and a second end of said inner layer, once deployed in the vessel at the site of the defect at least a portion of said outer layer surrounding at least a portion of said inner layer so that at least some of said loops of said outer layer overlap and contact at least some of said loops of said inner layer no more than twice for each of said loops, said IFM having a deployed diameter of between about 1.5 and about 12 mm, wherein said outer layer and said inner layer are connected to form a continuous strand, and wherein said first end of said outer layer is connected to said second end of said inner layer to form a loop;

said first catheter having a proximal end, a distal end, and a central lumen extending axially therethrough, said lumen having an inside diameter of between about 0.004 and about .006 inches to receive the pre-deployed configuration of said IFM such that said IFM is axially slidable therethrough; and a second catheter having a distal end, a proximal end, and a central lumen extending axially therethrough, said lumen of said second catheter having an inside diameter of at least about 0.022 inches to receive said first catheter such that said first catheter is axially slidable therein, and such that at least a portion of said distal end of said first catheter can be inserted into said lumen of said second catheter at said proximal end and passes through said lumen of said second catheter and exits said second catheter at said distal end.

* * * * *

UNITED STATES PATENT AND TRADEMARK OFFICE
CERTIFICATE OF CORRECTION

PATENT NO. : 6,190,402 B1
DATED : February 20, 2001
INVENTOR(S) : Joseph A. Horton, Dianna Joan Vincent It is certified that error appears in the above-identified patent and that said Letters Patent is hereby corrected as shown below:

Title page,
"References Cited", under "U.S. PATENT DOCUMENTS", add the following patents:

|   |   |   |   |
|---|---|---|---|
| -- | 4,629,458 | 12/1986 | Pinchuk |
|   | 4,670,286 | 06/1987 | Nyilas, et al. |
|   | 4,718,907 | 01/1988 | Karwoski, et al. |
|   | 4,795,458 | 01/1989 | Regan |
|   | 4,798,606 | 01/1989 | Pinchuk |
|   | 4,800,882 | 01/1989 | Gianturco |
|   | 4,813,925 | 03/1989 | Anderson, Jr. et al. |
|   | 4,820,298 | 04/1989 | Leveen, et al. |
|   | 4,856,516 | 08/1989 | Hillstead |
|   | 4,932,419 | 06/1990 | De Toldeo |
|   | 4,950,258 | 08/1990 | Kawai, et al. |
|   | 4,954,126 | 09/1990 | Wallsten |
|   | 4,990,155 | 02/1991 | Wilkoff |
|   | 5,035,706 | 07/1991 | Giantureo, et al. |
|   | 5,037,391 | 08/1991 | Hammerslag, et al. |
|   | 5,061,275 | 10/1991 | Wallesten, et al. |
|   | 5,071,407 | 12/1991 | Termin, et al. |
|   | 5,133,732 | 07/1992 | Wiktor |
|   | 5,141,502 | 08/1992 | Macaluso, Jr. |
|   | 5,147,370 | 09/1992 | McNamara, et al. |
|   | 5,151,105 | 09/1992 | Kwan-Gett |
|   | 5,163,952 | 11/1992 | Froix |
|   | 5,176,625 | 01/1993 | Brisson |
|   | 5,183,085 | 02/1993 | Timmermans |
|   | 5,222,969 | 06/1993 | Gillis |
|   | 5,314,472 | 05/1994 | Fontaine |
|   | 5,342,387 | 08/1994 | Summers |
|   | 5,441,516 | 08/1995 | Wang, et al. |
|   | 5,500,013 | 03/1996 | Buscemi, et al. |
|   | 5,514,176 | 05/1996 | Bosley, Jr. |

UNITED STATES PATENT AND TRADEMARK OFFICE
CERTIFICATE OF CORRECTION

PATENT NO. : 6,190,402 B1
DATED : February 20, 2001
INVENTOR(S) : Joseph A. Horton, Dianna Joan Vincent It is certified that error appears in the above-identified patent and that said Letters Patent is hereby corrected as shown below:

| | | |
|---|---|---|
| 5,523,092 | 06/1996 | Hanson, et al. |
| 5,540,713 | 07/1996 | Schnepp-Pesch, et al. |
| 5,562,641 | 10/1996 | Flomenblit, et al. |
| 5,601,593 | 02/1997 | Freitag |
| 5,603,694 | 02/1997 | Brown, et al. |
| 5,607,445 | 03/1997 | Summers |
| 5,674,277 | 10/1997 | Freitag |
| 5,676,697 | 10/1997 | McDonald |
| 5,693,085 | 12/1997 | Buirge, et al. |
| 5,702,373 | 12/1997 | Samson |
| 5,713,907 | 02/1998 | Hogendijk, et al. |
| 5,749,918 | 05/1998 | Hogendijk, et al. |
| 5,824,053 | 10/1998 | Khosravi, et al. |
| 5,824,059 | 10/1998 | Wiljay |
| 5,830,229 | 11/1998 | Konya, et al. |
| 5,980,514 | 11/1998 | Kupiecki, et al. --. |

Signed and Sealed this

Sixth Day of November, 2001

Attest:

NICHOLAS P. GODICI
Attesting Officer
Acting Director of the United States Patent and Trademark Office